United States Patent [19]

Perricone

[11] Patent Number: 5,554,647
[45] Date of Patent: Sep. 10, 1996

[54] METHOD AND COMPOSITIONS FOR TREATMENT AND/OR PREVENTION OF SKIN DAMAGE AND AGING

[76] Inventor: Nicholas V. Perricone, 35 Pleasant St. 0 Suite 2A, Meriden, Conn. 06450

[21] Appl. No.: 435,944

[22] Filed: Apr. 27, 1995

Related U.S. Application Data

[63] Continuation-in-part of Ser. No. 407,413, Mar. 17, 1995, which is a continuation-in-part of Ser. No. 24,890, Mar. 1, 1993, Pat. No. 5,409,693, which is a continuation of Ser. No. 732,444, Jul. 18, 1991, abandoned, which is a continuation of Ser. No. 420,287, Oct. 12, 1989, abandoned.

[51] Int. Cl.$^6$ .................................................. A61K 31/34
[52] U.S. Cl. ........................................... 514/474; 514/847
[58] Field of Search ........................................ 514/474, 847

[56] References Cited

U.S. PATENT DOCUMENTS

| | | | |
|---|---|---|---|
| 4,590,067 | 5/1986 | Meisner | 424/54 |
| 4,647,453 | 3/1987 | Meisner | 424/54 |
| 4,772,591 | 9/1988 | Meisner | 424/54 |
| 4,818,521 | 4/1989 | Tamabuchi | 514/474 |
| 4,938,696 | 7/1990 | Schinitsky | 514/474 |
| 5,391,373 | 2/1995 | Mausner | 424/401 |

FOREIGN PATENT DOCUMENTS

| | | | |
|---|---|---|---|
| 45-23634 | 8/1970 | Japan | 514/474 |
| 51-73137 | 6/1976 | Japan | 514/458 |
| 0116618 | 6/1985 | Japan | 514/474 |
| 1152613 | 7/1986 | Japan | 514/474 |
| 4686628 | 9/1975 | U.S.S.R. | 514/474 |

OTHER PUBLICATIONS

Block, G., Nutr. Rev. 50:207–213 (1992).
Jacob, R., A., et al., Am. J. Clin. Nutr. 54:1302S–9S (1991).
Meadows, G. G., et al., Am. J. Clin. Nutr. 54:1284S–91S (1991).
Perricone, N., J. Ger. Derm. 1:5–10 (1993).
Smart, R. C., and Crawford, C. L., Am. J. Clin. Nutr. 54:1266S–73S (1991).

*Primary Examiner*—Shelley A. Dodson
*Attorney, Agent, or Firm*—St. Onge Steward Johnston & Reens

[57] ABSTRACT

One or more precursors of acetylcholine such as dimethylaminoethanol in a dermatologically acceptable carrier is a topical treatment for aging skin and muscles. Preferred compositions also contain ascorbic acid or an ascorbic acid derivative, preferably a fatty acid ester of ascorbic acid such as ascorbyl palmitate. Optionally, other cofactors and agents affecting neurotransmitter synthesis such as vitamin $B_6$, pantothenic acid, calcium pantothenate, zinc, and/or tyrosine are included in the formulation. Other antioxidants such as vitamin E acetate or sorbate, or tocotrienols may also be employed in the composition.

20 Claims, No Drawings

METHOD AND COMPOSITIONS FOR TREATMENT AND/OR PREVENTION OF SKIN DAMAGE AND AGING

RELATED APPLICATION DATA

This is a continuation-in-part of U.S. application Ser. No. 08/407,413, filed Mar. 17, 1995, which was a continuation-in-part of U.S. application Ser. No. 08/024,890, filed Mar. 1, 1993 (scheduled to issue as U.S. Pat. No. 5,409,693 on Apr. 25, 1995), which is hereby expressly incorporated herein in its entirety by reference), which was a continuation of U.S. application Ser. No. 07/732,444, filed Jul. 18, 1991 (now abandoned), which was a continuation of U.S. application Ser. No. 07/420,287, filed Oct. 12, 1989 (now abandoned).

TECHNICAL FIELD

This invention relates primarily to the treatment of skin and muscles, particularly for faces that have developed prominent lines such as the nasolabial folds, hanging of tissue from the mandibular region, and increased sagging of tissue around the eyes and other areas observed in aging and in other conditions such as myasthenia gravis. In addition, sagging pectoralis muscles result in sagging of the chest and breast. The invention concerns compositions and methods of treating the epidermis and subcutaneous muscles to ameliorate these changes, and improve the external appearance.

BACKGROUND OF THE INVENTION

With age, the epidermis thins and the skin appendages atrophy. Hair becomes sparse and sebaceous secretions decrease, with consequent susceptibility to dryness, chapping, and fissuring. The dermis diminishes with loss of elastic and collagen fibers.

Sunlight exposure wreaks far greater destruction on the skin than time itself, and intensifies and augments the aging process. Free radical damage to the surface of the skin from sun exposure is manifested as lines, mottling, discoloration, precancers and cancers. Aging of both skin and other tissues is, in part, the result of constant free radical damage to cell membranes, leading to decreased cell function. This results in accumulation of waste products in the cells, such as lipofuscin; increase in the potassium content of the cells, which results in dehydration of the cells; and decreased production of messenger RNA and proteins.

In addition to changes on the surface of the skin due to the effects of gravity, muscles lengthen and give a sagging appearance to the skin because underlying muscle is looser. Current treatments of placid skin and muscles from aging typically involve plastic surgery. The plastic surgeon cuts the skin and muscle and then pulls it taut, reducing some of the tissue and discarding it, then suturing it so that the facial, chest and/or buttocks muscles remain tight. Treatment of sun-damaged and aged skin consists primarily of applications of various creams, lotions and gels to add moisture to the skin, as well as various acid peels to retexture the skin.

Cell age is due in part to free radical damage, which takes place mostly within the cell membrane. The cell membrane is most susceptible to attack to free radicals because of its dense molecular structure largely comprising lipids and lipoproteins, which are easily oxidized by reactive oxygen species. In the epidermis, reactive oxygen species, such as singlet oxygen, the superoxide anion, and hydroxyl radicals, and other free radicals are generated in normal metabolism, as well as through ultraviolet sun exposure, other forms of radiation, other environmental factors such as pollution or exposure to chemicals in the home or workplace, and the like. In addition, free radicals can activate chemical mediators of inflammation, particularly where arachadonic acid is released, which is then oxidized via two predominant pathways to produce either prostaglandins or leukotrines.

The body contains an endogenous antioxidant defense system made up of antioxidants such as vitamin E, vitamin C, superoxide dismutase, and glutathione. When metabolism increases or the body is subjected to other stress such as extreme exercise, radiation (ionizing and non-ionizing), or chemicals, the endogenous antioxidant systems are overwhelmed, and free radical damage takes place. Over the years, the cell membrane continually receives damage from reactive oxygen species and other free radicals, resulting in cross-linkage or cleavage of proteins and lipoproteins, and oxidation of membrane lipids and lipoproteins. Damage to the cell membrane can result in myriad changes including loss of cell permeability, increased intercellular ionic concentration, and decreased cellular capacity to excrete or detoxify waste products. As the intercellular ionic concentration of potassium increases, colloid density increases and m-RNA and protein synthesis are hampered, resulting in decreased cellular repair. Some cells become so dehydrated they cannot function at all.

In aging, the regularity of tissue structure is lost, and individual cells enlarge, but the total number of cells decreases approximately 30%. Intercellular collagen and elastin increases. The proportion of soluble collagen decreases and there may be increased cross-linking between long-chain collagen macromolecules. Elastin loses its discrete structure and elasticity and has an increased calcium content.

The external appearance of aging individuals is affected not only by changes in the epidermis, but also by subcutaneous changes in underlying muscle tissue. The combination of sagging muscles and aging skin contributes to the overall cosmetic changes typically observed, such as wrinkling, which involves the transition of a formerly smooth skin surface to one that appears unevenly shrunk and/or contracted. When muscles are at rest, a certain amount of tautness usually remains. The residual degree of contraction in skeletal muscles is called muscle tone. In aging individuals, the degree of contraction relaxes, and is particularly obvious in the face.

In order for a muscle to contract, a message is sent from the brain to the spinal cord, and then from the spinal cord to the skeletal muscles. This is accomplished by an action potential which travels down the axon of the nerve. The nerve ends at an area called the synaptic knob, and this action potential causes the synaptic knob to release small diffusible chemical neurotransmitters into the synaptic cleft. The synaptic knob is rich in tiny vesicles containing neurotransmitters, and these vesicles are rich in acetylcholine in knobs innervating muscles. Acetylcholine is released into the synaptic cleft, and then meets the muscle at an invagination called the synaptic gutter. This acetylcholine then finds receptors on the muscle surface, which causes the muscle to become permeable to sodium ions, which result in membrane potential increases in the local area of the end plate, about 75 millivolts, creating a local potential called the end plate potential. This causes the muscle to contract.

Once this contraction takes place, the remaining acetylcholine in the cleft is destroyed by an enzyme called cholinesterase. The choline is reabsorbed by the pre-synaptic knob to be used again to synthesize acetylcholine. Thus, it is at this neuromuscular junction where acetylcholine causes its effect. The synaptic knobs have the capability of continually synthesizing new transmitter substance. This occurs mainly in the cytoplasm of the synaptic knobs, and then it is absorbed into tiny vesicles and stored as needed.

It can be seen that neurotransmission at neuromuscular junctions is a complicated process affected by many factors including the biosynthesis of the neurotransmitter, storage of the neurotransmitter, release of the neurotransmitter, interaction of the neurotransmitter with receptors on effector cells, and termination of neurotransmitter activity by reuptake and/or metabolic processes.

In the production of acetylcholine, dimethylaminoethanol provides an excellent source of raw materials. Dimethylaminoethanol rapidly traverses cell membranes, and can, in fact, even cross the blood/brain barrier. Thus, dimethylaminoethanol provides not only precursors for the production of acetylcholine, but also allows rapid diffusion of these precursors into the synaptic knob, where acetylcholine is synthesized. In addition, the presence of dimethylaminoethanol may affect the activity of acetylcholinesterase in the destruction of acetylcholine in the synaptic cleft, providing more stimulus to muscle.

The aging process results in damage to presynaptic knobs, and therefore fewer neurotransmitters become available to a muscle for contraction. Receptor sites on muscle also deteriorate, and are unable to respond to the levels of acetylcholine present. Muscle tone maintained by nerve fibers releasing acetylcholine to small areas of muscle decreases, so that an appearance of sagging is observed.

It would be desirable to reverse or diminish these effects of aging without cosmetic surgery, and to treat other conditions exhibiting sagging facial muscles such as myasthenia gravis.

SUMMARY OF THE INVENTION

It is an object of this invention to provide a method and composition for treating aged skin and sagging muscles.

It is another and more specific object of the invention to provide a topical composition and method for shortening subcutaneous muscles, resulting in a lift in tissue on the face, chest or other area of application, while at the same time improving the overall condition of the skin.

These and other objects are accomplished by the present invention, which provides a method and composition for the topical treatment of aging skin and muscles. A formulation containing an effective amount of an acetylcholine precursor in a dermatologically acceptable carrier is applied to affected skin areas. In preferred embodiments, ascorbic acid or an ascorbic acid derivative such as a fatty acid ester is included in the topical composition. In many embodiments, the fatty acid ester is ascorbyl palmitate and the acetylcholine precursor is dimethylaminoethanol. Preferred embodiments also contain at least one other substance that enhances neurotransmitter synthesis such as pyridoxine (vitamin $B_6$), calcium pantothenate, pantothenic acid, zinc, tyrosine, or mixtures of any of these, and another antioxidant such as vitamin E acetate or sorbate, tocotrienol, ascorbic acid, or mixtures of any of these.

In one embodiment, the composition contains from about B to about 10 weight %, more narrowly about 7%, ascorbyl palmitate; from about 2 to about 5 weight %, more narrowly about 3%, dimethylaminoethanol; from about 1 to about 3 weight %, more narrowly about 2%, vitamin E acetate; from about 0.25 to about 1 weight %, more narrowly about 0.5%, pyridoxine; from about 0.5 to about 1.5 weight %, more narrowly about 1%, zinc in zinc sulfate; from about 1 to about 2 weight % pantothenic acid or calcium pantothenate; and from about 1 to about 3 weight %, more narrowly about 2%, tyrosine.

DETAILED DESCRIPTION OF THE INVENTION

This invention is based upon the surprising finding that aging skin and muscles can be treated by the topical application of a precursor of the neurotransmitter, acetylcholine, such as dimethylaminoethanol. Preferred topical compositions also contain ascorbic acid or an ascorbic acid derivative such as a fatty acid ester, e.g., ascorbyl palmitate. Other precursors of acetylcholine, substances that enhance neurotransmitter synthesis, particularly those that enhance neurotransmitter synthesis in the parasympathetic system, and additional antioxidants augment the efficacy of the topical composition.

In accordance with the present invention, at least one precursor of acetylcholine, preferably in association with a dermatologically acceptable carrier in which the precursor is dispersed or solubilized, is topically applied in effective amounts to skin areas which have been aged, or which are susceptible to age. As will be discussed in greater detail below, in preferred embodiments, ascorbic acid or an ascorbic acid derivative such as a fatty acid ester, is applied in admixture with the acetylcholine precursor. In some embodiments, the fatty acid ester is ascorbyl palmitate and the acetylcholine precursor is dimethylaminoethanol. Preferred compositions further contain at least one additional substance that enhances neurotransmitter synthesis such as pyridoxine, calcium pantothenate, zinc, tyrosine, and mixtures of any of these, and another antioxidant such as vitamin E acetate or sorbate, tocotrienol, ascorbic acid, or mixtures of any of these.

By the term "acetylcholine precursor" is meant any precursor in the biosynthetic pathway of acetylcholine, or related pathways. These include co-factors and precursors of acetylcholine, synthetic enzymes and precursors or enhancers of acetylCoA production. Acetylcholine precursors include, but are not limited to, dimethylaminoethanol, monoaminoethanol, choline, serine, and mixtures thereof. As used herein, "precursors" also include derivatives of precursors such as esters, e.g., acetic acid and para-chlorophenylacetic acid esters of dimethylaminoethanol or monoaminothanol, and the like. Folic acid and vitamin $B_{12}$ augment acetylcholine synthesis in some embodiments. Other embodiments contain choline acetylase agonists and acetylcholinesterase inhibitors to augment acetylcholine synthesis. Dimethylaminoethanol is a preferred precursor.

Acetylcholine precursors are typically used in topical compositions with ascorbic acid (vitamin C) and/or an ascorbic acid derivative or precursor. Derivatives include, but are not limited to, salts such as the sodium or calcium salt of ascorbic acid, ascorbic acid anhydride and ascorbic acid esters, or mixtures of any of these. Fatty acid esters are preferred. As used herein, the term "fatty acid esters of ascorbic acid" include any saturated or unsaturated fatty acid ester of ascorbic acid and mixtures of these esters. Because of their lack of susceptibility to oxidation and the development of off-odors in stored compositions, saturated fatty acid esters of ascorbic acid are especially preferred. These include, but are not limited to, ascorbyl palmitate, ascorbyl laurate, ascorbyl myristate, ascorbyl stearate, and mixtures thereof. Ascorbyl palmitate is employed in one embodiment. "Ascorbyl palmirate" includes the pure compound and esters enriched with ascorbyl palmirate such as those obtained by acylating ascorbic acid with fatty acids from feedstock oils or feedstock oil fractions containing primarily palmitic acid.

The amount of the acetylcholine precursor and, optionally, fatty acid ester of ascorbic acid, necessary to bring about the therapeutic treatment of the skin and subcutaneous muscle is not fixed per se, and necessarily is dependent upon the severity and extent of the aged tissue, the particular acetylcholine precursor employed, the particular ascorbyl fatty acid ester used in combination with the precursor, and additional antioxidants and agents affecting neurotransmitter synthesis employed, and the concentrations of these ingredients in the formulation put together in association with a dermatologically acceptable carrier.

Compositions of the invention are applied in admixture with a dermatologically acceptable carrier or vehicle (e.g., as a lotion, cream, ointment, soap, or the like). Topical application is facilitated and, in some cases, additional therapeutic effects are provided as might be brought about, e.g., by moisturizing of the affected skin areas. When a carrier is employed, it is necessary that the carrier be inert in the sense of not bringing about a deactivation of the ascorbic acid or ascorbic acid derivative or the acetylcholine precursor, and in the sense of not bringing about any adverse effect on the skin to which it is applied.

Suitable carriers include water, alcohols, oils and the like, chosen for their ability to dissolve or disperse the active ingredients at concentrations of active ingredients most suitable for use in the therapeutic treatment. Generally, even low concentrations of active ingredients in a carrier will be suitable, requiring only that more frequent topical application be resorted to. As a practical matter, however, to avoid the need for repeated application, it is desirable that the topically applied composition (e.g., ascorbyl fatty acid ester plus acetylcholine precursor in a carrier) be formulated to contain at least about 0.25% by weight, more preferably at least about 2% by weight, and most preferably at least about 7% by weight, of the ascorbyl fatty acid ester and at least about 0.25% by weight, more preferably at least about 1% by weight, and most preferably at least about 5% by weight, of the acetylcholine precursor, and accordingly, carriers will be chosen which can solubilize or disperse the active ingredients at such concentrations.

Preferred compositions of the invention contain at least one additional substance that enhances neurotransmitter synthesis such as pyridoxine, folic acid, vitamin $B_{12}$, calcium pantothenate, pantothenic acid, zinc, tyrosine, and mixtures of any of these, and another antioxidant such as vitamin E, vitamin E acetate, vitamin E sorbate, vitamin E succinate, tocotrienol, ascorbic acid, or mixtures of any of these. The formulation can also contain additional ingredients such as membrane stabilizers.

In one embodiment, the composition contains from about 5 to about 10 weight %, more narrowly about 7%, ascorbyl palmitate; from about 2 to about 5 weight %, more narrowly about 3%, dimethylaminoethanol; from about 1 to about 3 weight %, more narrowly about 2%, vitamin E acetate; from about 0.25 to about 1 weight %, more narrowly about 0.5%, pyridoxine; from about 0.5 to about 1.5 weight %, more narrowly about 1%, zinc in zinc sulfate; from about 1 to about 2 weight % pantothenic acid or calcium pantothenate (expressed as pantothenate), and from about 1 to about 3 weight %, more narrowly about 2%, tyrosine.

In some embodiments, the compositions contain tocotrienols or derivatives thereof for enhanced therapeutic or prophylactic treatment as described in U.S. Pat. No. 5,376,361 to Perricone (which is hereby incorporated herein in its entirety by reference). These are particularly advantageous because tocotrienols are oily so that they physically contributes to the lubrication and soothing of affected skin areas. Reductive agents such as α-hydroxy acids can, optionally, be utilized with the tocotrienols for a means for yet further enhancing the efficacy of the compositions. Glycolic acid is preferred in one embodiment.

As used herein, the term "tocotrienol" encompasses tocopherols bearing unsaturated tails, including, but not limited to, naturally occurring α-, β-, γ-, and δ- tocotrienols, desmethyl-tocotrienol, didesmethyl-tocotrienol, their synthetic counterparts, their counterparts having methylated or demethylated chroman rings, stabilized derivatives such as those having the phenolic hydroxyl functionality acylated with an organic acid to form an ester such as acetates and succinates, and mixtures thereof. The term also includes tocotrienol-enriched fractions and tocotrienol-enriched vitamin E preparations.

Where tocotrienols are employed, the amount of tocotrienol or one or more derivatives thereof (hereinafter referred to collectively as tocotrienol for ease of reference) necessary to bring about enhanced prevention and/or therapeutic skin treatment in conjunction with acetylcholine precursors (and optionally ascorbic acid and/or a derivative) is not fixed per se, and necessarily is dependent upon the identity and form of tocotrienol employed, the concentration of tocotrienol when employed as a tocotrienol-enriched vitamin E preparation and/or with a carrier, the amount and type of ascorbyl fatty acid ester, the user's skin type, and, where present, the severity and extent of the patient's pathological skin condition. Many embodiments contain from about 0.025% to 0.25% tocotrienol.

While the carrier for the acetylcholine precursor, and optionally, ascorbic acid or an ascorbic acid derivative such as a fatty acid ester can consist of a relatively simple solvent or dispersant such as water or oils, it is generally preferred that the carrier comprise a composition more conducive to topical application, and particularly one which will form a film or layer on the skin to which it is applied so as to localize the application and provide some resistance to perspiration and/or one which aids in percutaneous delivery and penetration of the active ingredients into lipid layers. Many such compositions are known in the art, and can take the form of lotions, creams, gels or even solid compositions (e.g., stick-form preparations). Typical compositions include lotions containing water and/or alcohols and emollients such as hydrocarbon oils and waxes, silicone oils, hyaluronic acid, vegetable, animal or marine fats or oils, glyceride derivatives, fatty acids or fatty acid esters or alcohols or alcohol ethers, lanolin and derivatives, polyhydric alcohols or esters, wax esters, sterols, phospholipids and the like, and generally also emulsifiers (nonionic, cationic or anionic), although some of the emollients inherently possess emulsifying properties. These same general ingredients can be formulated into a cream rather than a lotion, or into gels, or into solid sticks by utilization of different proportions of the ingredients and/or by inclusion of thickening agents such as gums or other forms of hydrophillic colloids. Such compositions are referred to herein as dermatologically acceptable carriers. Most preferred for skin are those carriers which are fat-soluble, i.e., those which can effectively penetrate skin layers and deliver the active ascorbyl fatty acid ester to the lipid-rich layers of the skin.

Though lecithin may be an ingredient in the topical compositions of the invention., lecithin-based carriers per se such as those disclosed by Simon in U.S. Pat. No. 5,401,728 are generally not preferred. Though lecithin-based topicals have been employed for years because phosphatidyl choline softens skin, the size of the molecule is prohibitively large and decreases the bioavailability of active ingredients.

Generally, the composition is topically applied to the affected skin areas in a predetermined or as-needed regimen to bring about improvement, it generally being the case that gradual improvement is noted with each successive application. Insofar as has been determined based upon clinical studies to date, no adverse side effects are encountered.

In an assessment of the efficacy of a composition of the invention, an aqueous suspension made up of approximately 7% by weight ascorbyl palmirate, 3% dimethylaminoethanol, 2% by weight vitamin E acetate, ½% by weight of vitamin $B_6$ (pyridoxine), 1% by weight zinc sulfate (weighed as zinc), 1% by weight calcium pantothenate, and 2% by weight tyrosine is applied to facial skin. Within 3 to 5 minutes of application, the facial skin becomes more taut. A reduction of nasolabial folds is observed, as well as a general tightening of the face in the periorbital region and the forehead. This effect lasts for approximately 24 hours, and, when the formulation is reapplied on a daily basis, after about a month, there apears to be a marked shortening of muscle tissue resulting in a more youthful appearance. The formulation can also be placed on the pectoralis area and in the area of breast tissue, resulting in an uplifted look to that area. It can also be applied to the faces of myasthenia gravis patients to improve their appearance.

While not wishing to be bound to any theory, it is believed that treatment in accordance with the present invention helps prevent free radical damage to skin and helps reverse cell membrane damage by application of free radical scavengers and quenchers. In addition, by providing precursors of acetylcholine, muscle tone is increased and the resultant shortening of muscles lifts tissue on the face, chest, or other areas where the composition is applied.

The presence of dimethylaminoethanol, as well as other agents and co-factors involved in acetylcholine production and neurotransmitter synthesis, such as vitamin C, vitamin $B_6$ (pyridoxine), calcium pantothenate or pantothenic acid, and zinc, appears to help boost levels of acetylcholine in the neuromuscular junction, resulting in increased muscle tone. This increased muscle tone causes a slight shortening of the muscle, and over a period of time, the muscle actually does become shorter. A shorter muscle results in a lifting of overlying skin, with the cosmetic appearance of a diminishment of sagging. Other synapses of nerves interact with the involuntary muscles, as well as the sympathetic and parasympathetic nervous system, using a neurotransmitter called norepinephrine. As disclosed in U.S. Pat. Nos. 4,647,453 and 4,772,591 to Meisner, precursors of norepinephrine are the amino acids tyrosine, phenylalanine, and other cofactors such as pyridoxine, zinc, panothenic acid, and ascorbic acid. Having these precursors in the formula may enhance the effects at the neuromuscular junction, as the presence may affect the enzymatic destruction of choline as well as lead to increased tone by undiscovered mechanisms.

It is important to have free radical scavengers in the cell membrane that protect the target site and have a greater affinity for free radicals than the target tissue. As a free radical scavenger or neutralizer, ascorbyl palmitate, because Of its palmitic fatty acid side chain, intersperses in membranes more effectively, and therefore provides better protection for cell membranes during free radical attack. Substances that stabilize membranes or increase endogenous glutathione production further prevent free radical damage to the cell and membrane structures. In membranes, vitamin E also provides protection from free radical damage.

In addition, fatty acid esters of ascorbic acid such as ascorbyl palmitate aid or accelerate collagen synthesis, so as to remedy the depeleted collagen observed in aging. By virtue of its fat solubility, fatty acid esters of ascorbic acid enhance percutaneous delivery of acetylcholine precursors such as dimethylaminoethanol.

Dimethylaminoethanol also intersperses in cellular membranes, and acts as a free radical scavenger, especially for the hydroxyl radical. Again, while not wishing to be bound to any theory, but the special efficacy of the compositions of the invention may in part be due to three functions dimethylaminoethanol plays. It is a cellular antioxidant interspersing within lipid-rich membranes, a precursor of acetylcholine and a precursor of choline, which is used to synthesize phosopholipid cellular membranes. Dimethylaminoethanol can cross membranes, as well as the blood/brain barrier, and is superior to choline, which cannot cross cellular membranes to reach the site of membrane synthesis, as an acetylcholine precursor in the practice of the invention.

The application of free radical scavengers and topical antiflammatories with substances that cause a shortening of muscles, produces increased tone, provides a composition that enhances the appearance of the skin, and results in a smoother, tighter, and more youthful appearance for aging persons and patients afflicted with conditions that cause sagging faces such as myasthenia gravis.

Acetylcholine receptors are found on human epidermal keratinocytes. When these are occupied, they can affect keratinocyte growth, resulting in a more youthful appearance, enhancing the effects of compositions of the invention.

Having described the invention with reference to particular compositions, theories of effectiveness, and the like, it will be apparent to those of skill in the art that it is not intended that the invention be limited by such illustrative embodiments or mechanisms, and that modifications can be made without departing from the scope or spirit of the invention, as defined by the appended claims. The claims are meant to cover the claimed components and steps in any sequence which is effective to meet the objectives there intended, unless the context specifically indicates the contrary.

I claim:

1. A method for the treatment of aging skin and subcutaneous muscles comprising topically applying to affected skin areas a composition comprising an acetylcholine precursor active ingredient selected from the group consisting of dimethylaminoethanol, monoaminoethanol, choline, serine, acetic acid esters of dimethylaminoethanol, acetic acid esters of monoaminoethanol, para-chlorophenylacetic acid esters of dimethylaminoethanol, para-chlorophenylacetic acid esters of monoaminoethanol, and mixtures thereof in a dermatologically acceptable carrier that percutaneously delivers the active ingredient in amounts effective to produce increased muscle tone.

2. A method according to claim 1 wherein the acetylcholine precursor is dimethylaminoethanol.

3. A method according to claim 2 wherein the composition further comprises an effective amount of a fatty acid ester of ascorbic acid.

4. A method according to claim 3 wherein the fatty acid ester of ascorbic acid is ascorbyl palmitate.

5. A method according to claim 3 wherein the composition further comprises at least one additional substance that enhances neurotransmitter synthesis.

6. A method according to claim 5 wherein the composition further comprises at least one antioxidant.

7. A method according to claim 5 wherein the substance is selected from the group consisting of pyridoxine, calcium pantothenate, pantothenic acid, and mixtures thereof.

8. A method according to claim 7 wherein the composition further comprises zinc, tyrosine, or mixtures thereof.

9. A method according to claim 6 wherein the antioxidant is selected from the group consisting of ascorbic acid, vitamin E acetate, vitamin E sorbate, vitamin E succinate, tocotrienols, and mixtures of any of these.

10. A topical composition for the treatment of aging skin and muscles comprising a fat-soluble fatty acid ester of ascorbic acid a precursor of acetylcholine selected from the group consisting of dimethylaminoethanol, monoaminoethanol, choline, acetic acid esters of dimethylaminoethanol, acetic acid esters of monoaminoethanol, para-chlorophenylacetic acid esters of dimethylaminoethanol, para-chlorophenylacetic acid esters of monoaminoethanol, and mixtures thereof; and at least one substance that enhances neurotransmitter synthesis selected from the group consisting of pyridoxine, calcium pantothenate, pantothenic acid, zinc, tyrosine, and mixtures of any of these, in a dermatologically acceptable carrier.

11. A composition according to claim 10 wherein said fatty acid ester is ascorbyl palmitate and said precursor of acetylcholine is dimethylaminoethanol.

12. A composition according to claim 10 further comprising vitamin E or a vitamin E derivative selected from the group consisting of vitamin E, vitamin E acetate, vitamin E sorbate, vitamin E succinate, and mixtures thereof.

13. A composition according to claim 12 further comprising another antioxidant.

14. A composition according to claim 13 wherein the antioxidant is selected from the group consisting of vitamin C, tocotrienol, and mixtures of any of these.

15. A topical composition for the treatment of aging skin and muscles comprising a fatty acid ester of ascorbic acid; an acetylcholine precursor selected from the group consisting of dimethylaminoethanol, monoaminoethanol, and choline, and at least one other substance selected from the group consisting of pantothenic acid, calcium pantothenate, vitamin E, vitamin E acetate, vitamin E sorbate, vitamin E succinate, tocotrienol, vitamin $B_{12}$, folic acid, pyridoxine, zinc sulfate, tyrosine, glycolic acid, and mixtures of any of these.

16. A composition according to claim 15 wherein the fatty acid ester of ascorbic acid is ascorbyl palmitate and the acetylcholine precursor is dimethylaminoethanol.

17. A composition according to claim 16 comprising at least about 2% by weight ascorbyl palmitate and at least 1% by weight dimethylaminoethanol.

18. A topical composition for the treatment of aging skin and muscles comprising ascorbyl palmitate, dimethylaminoethanol, vitamin E acetate or sorbate, pantothenic acid or calcium pantothenate, pyridoxine, zinc sulfate, and tyrosine in a dermatologically acceptable carrier.

19. A composition according to claim 18 comprising from about 5 to about 10 weight % ascorbyl palmitate, from about 2 to about 5 weight % dimethylaminoethanol, from about 1 to about 3 weight % vitamin E acetate, from about 0.25 to about 1 weight % pyridoxine, from about 0.5 to about 1.5 weight % zinc in zinc sulfate, from about 1 to about 1 weight % calcium pantothenate, and from about 1 to about 3 weight % tyrosine.

20. A composition according to oclaim 19 comprising about 7 weight % ascorbyl palmitate, about 3 weight % dimethylaminoethanol, about 2 weight % vitamin E acetate, about 0.5% weight %, about 1 weight % zinc in zinc sulfate, and 2 weight % tyrosine.

\* \* \* \* \*